(12) United States Patent
Teoh et al.

(10) Patent No.: US 7,651,513 B2
(45) Date of Patent: Jan. 26, 2010

(54) FLEXIBLE EMBOLIC DEVICE DELIVERY SYSTEM

(75) Inventors: Clifford Teoh, Los Altos, CA (US);
Stephen C. Porter, Oakland, CA (US);
Kevin M. Jaeger, Pleasanton, CA (US);
Michael Wallace, Fremont, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1077 days.

(21) Appl. No.: 10/407,295

(22) Filed: Apr. 3, 2003

(65) Prior Publication Data

US 2004/0199175 A1 Oct. 7, 2004

(51) Int. Cl.
*A61M 25/01* (2006.01)
(52) U.S. Cl. .................. 606/200; 606/108; 606/194
(58) Field of Classification Search ............ 606/113, 606/127, 191–200, 119, 108; 623/1.11–1.54, 623/23.72; 128/897, 898
See application file for complete search history.

(56) References Cited

U.S. PATENT DOCUMENTS

| | | | |
|---|---|---|---|
| 4,867,173 A * | 9/1989 | Leoni ................ 600/585 |
| 4,994,069 A | 2/1991 | Ritchart et al. |
| 5,108,407 A | 4/1992 | Geremia et al. |
| 5,122,136 A | 6/1992 | Guglielmi et al. |
| 5,217,484 A | 6/1993 | Marks |
| 5,234,437 A | 8/1993 | Sepetka |
| 5,250,071 A | 10/1993 | Palermo |
| 5,261,916 A | 11/1993 | Engelson |
| 5,304,195 A | 4/1994 | Twyford, Jr. et al. |
| 5,350,397 A | 9/1994 | Palermo et al. |
| 5,354,295 A | 10/1994 | Guglielmi et al. |
| 5,423,829 A * | 6/1995 | Pham et al. ........ 606/108 |
| 5,540,680 A | 7/1996 | Guglielmi et al. |
| 5,624,449 A | 4/1997 | Pham et al. |
| 5,667,767 A | 9/1997 | Greff et al. |
| 5,669,905 A | 9/1997 | Scheldrup et al. |
| 5,690,671 A | 11/1997 | McGurk et al. |
| 5,695,480 A | 12/1997 | Evans et al. |
| 5,702,361 A | 12/1997 | Evans et al. |
| 5,795,331 A | 8/1998 | Cragg et al. |
| 5,830,178 A | 11/1998 | Jones et al. |
| 5,855,578 A | 1/1999 | Guglielmi et al. |
| 5,891,128 A * | 4/1999 | Gia et al. .............. 606/1 |
| 5,891,130 A | 4/1999 | Palermo et al. |
| 5,895,385 A | 4/1999 | Guglielmi et al. |
| 5,916,235 A | 6/1999 | Guglielmi |

(Continued)

OTHER PUBLICATIONS

PCT International Search Report for PCT/US2004/009364, Applicant: Scimed Life Systems, Inc. Forms PCT/ISA/210 and 220, dated Oct. 18, 2004 (9 pages).

(Continued)

*Primary Examiner*—Ahntuan T Nguyen
*Assistant Examiner*—Kathleen Sonnett
(74) *Attorney, Agent, or Firm*—Vista IP Law Group LLP (57) ABSTRACT

The present invention provides an embolic assembly delivery apparatus having superior flexibility characteristics at its distal end, that is, at the point of attachment of the embolic assembly to the delivery apparatus. It also provides a method of using the apparatus to deliver an embolic assembly to a target site in a patient's body.

16 Claims, 2 Drawing Sheets

U.S. PATENT DOCUMENTS

| | | | |
|---|---|---|---|
| 5,925,037 | A | 7/1999 | Guglielmi et al. |
| 5,925,062 | A | 7/1999 | Purdy |
| 5,928,226 | A | 7/1999 | Guglielmi et al. |
| 5,935,148 | A | 8/1999 | Villar et al. |
| 5,941,888 | A * | 8/1999 | Wallace et al. .............. 606/108 |
| 5,944,714 | A | 8/1999 | Guglielmi et al. |
| 5,947,962 | A | 9/1999 | Guglielmi et al. |
| 5,947,963 | A | 9/1999 | Guglielmi |
| 5,964,797 | A | 10/1999 | Ho |
| 5,976,126 | A | 11/1999 | Guglielmi |
| 5,984,929 | A | 11/1999 | Bashiri et al. |
| 6,010,498 | A | 1/2000 | Guglielmi |
| 6,017,977 | A | 1/2000 | Evans et al. |
| 6,059,779 | A | 5/2000 | Mills |
| 6,063,070 | A | 5/2000 | Eder |
| 6,063,104 | A | 5/2000 | Villar et al. |
| 6,066,133 | A | 5/2000 | Guglielmi et al. |
| 6,077,260 | A | 6/2000 | Wheelock et al. |
| 6,083,220 | A | 7/2000 | Guglielmi et al. |
| 6,086,577 | A | 7/2000 | Ken et al. |
| 6,146,373 | A | 11/2000 | Cragg et al. |
| 6,156,061 | A | 12/2000 | Wallace et al. |
| 6,165,178 | A | 12/2000 | Bashiri et al. |
| 6,193,708 | B1 | 2/2001 | Ken et al. |
| 6,231,573 | B1 | 5/2001 | Amor et al. |
| 6,281,263 | B1 | 8/2001 | Evans et al. |
| 6,303,100 | B1 | 10/2001 | Ricci et al. |
| 6,342,202 | B1 | 1/2002 | Evans et al. |
| 6,344,041 | B1 | 2/2002 | Kupiecki et al. |
| 6,397,850 | B1 | 6/2002 | Scheldrup et al. |
| 6,425,893 | B1 | 7/2002 | Guglielmi |
| 7,238,194 | B2 * | 7/2007 | Monstadt et al. ............ 606/198 |
| 2004/0078050 | A1 * | 4/2004 | Monstadt et al. ............ 606/191 |

OTHER PUBLICATIONS

PCT Written Opinion of the International Search Authority for PCT/US2004/009364, Applicant: Scimed Life Systems, Inc, Form PCT/ISA/237, dated Oct. 18, 2004 (6 pages).

* cited by examiner

FLEXIBLE EMBOLIC DEVICE DELIVERY SYSTEM

BACKGROUND OF THE INVENTION

The use of embolic devices to prevent rupture, or to minimize blood loss in case of rupture, of aneurysms has become a relatively routine medical procedure. The basic approach is to deliver the device to the site of an aneurysm using a steerable catheter that is inserted in a vessel at a remote location and is then directed to a position adjacent to the aneurysm. A pusher wire, with the embolic device attached to its distal end, is then threaded through the catheter and beyond until the device is situated in the aneurysm. The presently preferred embolic device is a coil of wire, typically platinum/tungsten alloy, that when stretched assumes a linear helical configuration and when relaxed assumes a convoluted configuration that will fill the interior of the aneurysm. The convoluted configuration may be completely random or it may be controlled using shape-memory alloys. The wire generally has a diameter of 2-6 mils while the coils are usually in the range of 10-30 mils in diameter. The coils may be of any length appropriate for the intended use. Depending on its size, from one to a great many coils may used to fill a single aneurysm. Once in place, the embolic devise initiates formation of a thrombus that is soon complemented by a collagenous material that further lessens the potential for rupture or for significant blood loss should the aneurysm break.

Once a coil is in place in the aneurysm, it is detached from the distal end of the pusher wire. Detachment can be accomplished in numerous ways including mechanically (unscrew, remove key from slot, separate ball and socket, etc.), electrolytically (disintegration of junction between metals having different standard electrode potentials) and energetically (vibrational cohesive disruption). Electrolytic detachment is one of the currently favored method of releasing an embolic device due it lack of a need for complex remote manipulation of the connection and, therefore, its speed and precision.

In virtually all electrolytically separable embolic device delivery systems presently in use, the embolic device is attached essentially to the end of the pusher wire, the difference in electrode potential between the pusher wire metal and that of which the embolic device is constructed supplying the requisite potential. The pusher wire, however, is generally relatively stiff, a necessary characteristic that allows it to be controllably threaded through the catheter and beyond to position the embolic device at the target site.

While the current devices work well, certain advantages might accrue if the distal end of the device were somewhat more flexible than the pusher wire itself. For instance, without limitation, some operators might find that such a device provides a softer feel as the embolic device is positioned and released. This invention provides such a flexible device.

SUMMARY OF THE INVENTION

Thus, in one aspect, the present invention, a device for releasing an embolic assembly at a target site in a vessel of a patient, comprising:

a core wire comprising a first electrically-conductive substance that is at least partially fixedly encased in a first non-conductive substance and has a proximal and a distal end, its proximal end being connected to an electrical signal generator;

a flexible member having a proximal and a distal end, its proximal end being coupled to the distal end of the core wire;

an embolic assembly having a proximal and a distal end, its proximal end being operatively coupled to the distal end of the flexible member; and, an electrolytic detachment site located between the proximal end of the embolic assembly and a distal end of the first non-conductive substance.

In an aspect of this invention the flexible member comprises a second wire comprising a second electrically-conductive substance, which may be the same as, or different than, the first electrically-conductive substance, the second wire having a helical coil segment and, distal to the helical coil segment, a straight segment; wherein the helical coil segment is fixedly coupled to the distal end of the core wire and is also fixedly encased in the first non-conductive substance and at least a portion of the straight segment is bare, the bare portion being coupled to a proximal end of a third electrically-conductive substance, which is different from the second electrically-conductive substance, the third electrically conductive substance having a distal end that is operatively coupled to the embolic assembly.

In an aspect of this invention, the third electrically-conductive substance is, along with the proximal end of the embolic assembly, encased in a non-conductive substance that may be the same as, or different than, the first non-conductive substance.

In an aspect of this invention, the third electrically-conductive substance comprises an electrically conductive wire that is fixedly helically wound around the bare portion of the straight segment of the second wire.

In an aspect of this invention, the helically wound segment of the second wire comprises a first and a second helically wound portion, the portions being independently open- or closed-pitched, the first portion being at least partially fixedly encased in the first non-conductive substance and being coupled to the distal end of the core wire, the second portion optionally being partially encased in the first non-conductive substance, the second portion being distal to the first portion and coupled to the third electrically-conductive substance.

In an aspect of this invention, the first and second portions of the helically-wound segment are both closed pitched.

In an aspect of this invention, the first and second portions of the helically-wound segment are both open-pitched.

In an aspect of this invention, the first portion of the helically wound segment is open-pitched and the second portion is closed-pitched.

In an aspect of this invention, the second portion of the helically-wound segment is at least partially surface-coated with a second non-conductive substance, which may be the same as, or different from, the first non-conductive substance.

In an aspect of this invention, the core wire comprises stainless steel or nitinol; the first non-conductive substance comprises a first non-conductive polymer; the second wire independently comprises stainless steel or nitinol and the third electrically-conductive substance comprises a platinum-tungsten alloy.

In an aspect of this invention, the core wire comprises stainless steel or nitinol; the first non-conductive substance comprises a first non-conductive polymer; the second wire independently comprises stainless steel or nitinol; the third electrically-conductive substance comprises a platinum-tungsten alloy and the second non-conductive substance comprises a second non-conductive polymer, which may be the same as, or different from, the first non-conductive polymer.

In an aspect of this invention, the flexible member comprises a first loop having a first and a second end, both of which are operatively coupled to the distal end of the core wire, a distal portion of which is optionally bare and a second loop having a first and a second end, both of which are operatively coupled to the proximal end of the embolic assembly, wherein the first and second loops are interlinked.

In an aspect of this invention, the first and second ends of the first loop are operatively coupled to a bare portion of the distal end of the core wire by a second electrically-conductive substance that is different from the first electrically-conductive substance, the second electrically-conductive substance having a proximal end fixedly coupled to the distal end of the bare portion of the core wire and a distal end that, along with the two ends of the first loop, is fixedly encased in a second non-conductive substance, which may be the same as, or different than, the first non-conductive substance.

In an aspect of this invention, the second electrically-conductive substance comprises an electrically conductive wire that is helically wound around the bare portion of the distal end of the core wire and the ends of the first loop.

In an aspect of this invention, the first electrically-conductive substance comprises stainless steel or nitinol; the first non-conductive substance comprises a first non-conductive polymer; the second electrically-conductive substance comprises a platinum-tungsten alloy and the second non-conductive substance comprises a second non-conductive polymer, which may be the same as, or different than, the first non-conductive polymer.

In an aspect of this invention the flexible member comprises a second wire comprising a second electrically-conductive substance, which may be the same as, or different than, the first electrically-conductive substance, and having a proximal and an distal end, the second wire further having, at its proximal end, a first helical coil segment and, at its distal end, a first loop segment, the helical coil segment being fixedly coupled to the distal end of the core wire and a third wire comprising a third conductive substance, which is different than the second conductive substance, and having a proximal and a distal end, the third wire further having a second loop segment at its proximal end, wherein the first and second loop segments are interlinked and the distal end of the second helical segment and the proximal end of the embolic assembly are fixedly encased in a second non-conductive substance.

In an aspect of this invention, the first and second conductive substances comprise stainless steel or nitinol; the first non-conductive substance comprises a first non-conductive polymer; the third conductive substance comprises a platinum-titanium alloy and the second non-conductive substance comprises a second non-conductive polymer, which may be the same as, or different than, the first non-conductive substance.

In an aspect of this invention, the above device(s) further comprises a stretch resistant member having a first and a second end, the first end being fixedly coupled to the distal end of the core wire and the second end being fixedly coupled to the flexible member.

In an aspect of this invention, the above device(s) further comprise a non-conductive bushing at a distal end of the first non-conductive substance, the bushing having a lumen through which the distal end of the core wire, or the distal end of a flexible member, passes.

An aspect of this invention is a method for releasing an embolic assembly at a target site in a patient's body, comprising:

providing a delivery member capable of positioning a core wire in close proximity to a target site, the delivery member comprising a first elongate tube having a proximal end, a distal end and an axial lumen;

providing a core wire slidably disposed within the axial lumen, the wire comprising a first electrically-conductive substance that is at least partially fixedly encased in a first non-conductive substance and has a proximal and a distal end, its proximal end being connected to an electrical signal generator;

providing a flexible member having a proximal and a distal end, its proximal end being coupled to the distal end of the core wire;

providing an embolic assembly having a proximal and a distal end, its proximal end being operatively coupled to the distal end of the flexible member; and, providing an electrolytic detachment site located between the proximal end of the embolic assembly and a distal end of the first conductive substance;

moving the delivery member to a position in close proximity to the target site;

sliding the core wire through the lumen of the delivery member until the embolic assembly is at or in the target site; and, sending an electrical signal to the electrolytic detachment site which results in release of the embolic assembly.

In an aspect of this invention, in the above method, the flexible member comprises a second wire comprising a second electrically-conductive substance, which may be the same as, or different than, the first electrically-conductive substance, the second wire having a helical coil segment and, distal to the helical coil segment, a straight segment wherein the helical coil segment is fixedly coupled to the distal end of the core wire and is also fixedly encased in the first non-conductive substance and at least a portion of the straight segment is bare, the bare portion being coupled to a proximal end of a third electrically-conductive substance, which is different from the second electrically-conductive substance, the third electrically conductive substance having a distal end that is operatively coupled to the embolic assembly.

In an aspect of this invention, in the above method, the third electrically-conductive substance comprises an electrically conductive wire that is fixedly helically wound around the bare portion of the straight segment of the second wire.

In an aspect of this invention, in the above method, the helically wound segment of the second wire comprises a first and a second helically wound portion, the portions being independently open- or closed-pitched, the first portion being at least partially fixedly encased in the first non-conductive substance and being coupled to the distal end of the core wire, the second portion optionally being partially encased in the first non-conductive substance, the second portion being distal to the first portion and coupled to the third electrically-conductive substance.

In an aspect of this invention, in the above method, the first and second portions of the helically wound segment are both closed-pitched.

In an aspect of this invention, in the above method, the first and second portions of the helically wound segment are both open-pitched.

In an aspect of this invention, in the above method, the first portion of the helically would segment is open-pitched and the second portion is closed-pitched.

In an aspect of this invention, in the above method, the second portion of the helically-wound segment is at least partially surface-coated with a second non-conductive substance, which may be the same as, or different from the first non-conductive substance.

In an aspect of this invention, in the above method, the flexible member comprises a first loop having a first and a second end, both of which are fixedly coupled to the distal end of the core wire, a distal portion of which is optionally bare and a second loop having a first and a second end both of which are operatively coupled to the proximal end of the embolic assembly wherein the first and second loops are interlinked.

In an aspect of this invention, in the above method, the first and second ends of the first loop are operatively coupled to a bare portion of the distal end of the core wire by a second electrically-conductive substance that is different from the first electrically-conductive substance, the second electrically-conductive substance having a proximal end fixedly coupled to the bare portion of the distal end of the core wire and a distal end that, along with the two ends of the first loop, is fixedly encased in a second non-conductive substance, which may be the same as, or different than, the first non-conductive substance.

In an aspect of this invention, in the above method, the flexible member comprises a second wire comprising a second electrically-conductive substance, which may be the same as, or different than, the first electrically-conductive substance, and having a proximal and an distal end, the second wire further having, at its proximal end, a first helical coil segment and, at its distal end, a first loop segment, the helical coil segment being fixedly coupled to the distal end of the core wire and a third wire comprising a third conductive substance, which is different than the second conductive substance, and having a proximal and a distal end, the third wire further having a second loop segment at its proximal end wherein the first and second loop segments are interlinked and the distal end of the second helical segment and the proximal end of the embolic assembly are fixedly encased in a second non-conductive substance.

In an aspect of this invention, the above method further comprises a stretch resistant member having a first and a second end, the first end being fixedly coupled to the distal end of the core wire and the second end being fixedly coupled to the flexible member.

In an aspect of this invention, the above method further comprises a non-conductive bushing coupled to a distal end of the first non-conductive substance and having a lumen through which the distal end of the core wire, or the distal end of the flexible member, passes.

In an aspect of this invention, the target site is selected from the group consisting of an aneurysm, an arteriovenous malformation, a fistula, a blood vessel or any other body lumen.

DETAILED DESCRIPTION OF THE INVENTION

Brief Description of the Figures

The figures and description of each of them below are intended solely to aid in the understanding of the invention herein. They are not intended, nor should they be construed, to limit the scope of this invention in any manner whatsoever. For example, where a helical coil is being represented, out of necessity only a certain number of actual turns can be shown. The number of turns shown, however, is not to be construed as limiting the scope of this invention in any manner whatsoever; more or less turns are possible and are within the scope of this invention. Also, the pitch of the helical coils is not limited to that shown in the figures. The pitch can be varied to impart any desired degree of flexibility to the segments of the device containing the coils.

In FIG. 2A, the proximal portion 520 is open-pitched and the distal portion 530 is closed-pitched.

DISCUSSION

Figure 1:
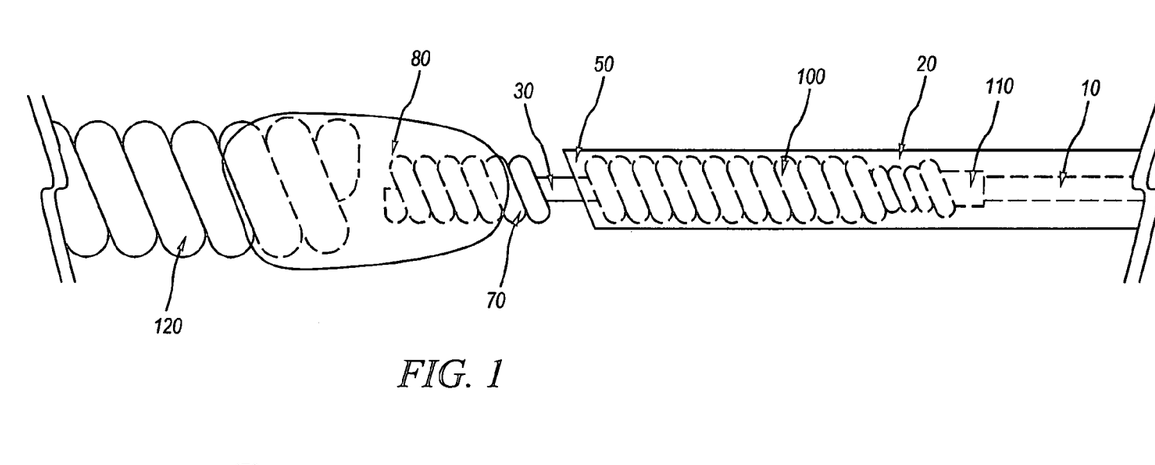
FIG. 1 is a schematic depiction of an embodiment of this invention wherein flexibility is introduced between the distal end of pusher wire 10 and embolic member 120 by helically wound wire 100.

FIG. 1 schematically depicts an embodiment of the present invention. The distal end of pusher (or core, the terms are used interchangeably herein) wire 10 is coupled to the proximal end of helical coil 100 by weld junction 110. Helical coil 100 may be open or closed pitch and the pitch itself can be varied to establish a desired degree of softness or pliability in region of the device. Pusher wire 10 is encased in non-conducting substance 20. Weld junction 110 and helical coil 100 are also encased in non-conductive substance 20. Weld junction 110 and helical coil 100 are also encased in non-conductive substance 20. Typically the non-conducting substance will encase wire 10 from near its proximal end (enough being left bare to connect to a power supply) to its distal end and then encase helical coil 100 to near its distal end, where a portion is left bare to provide detachment site 30 where electrolytic disintegration of the wire can occur resulting in separation of embolic member 120. Non-conducting substance 20 can be any suitable insulating material such as poly(tetrafluoroethylene) (Teflon®), poly(paraxylene) (Parylene®), poly(ethylene terephthalate) (PET), poly(cyanoacrylates) and the like. PET is presently preferred. Pusher wire 10 may be made of any material that has sufficient resilience/flexibility to permit accurate movement and placement of its distal end at a target site in a patient's body by manipulation of the wire at its proximal end, which may be many centimeters away. While this includes material such as carbon fiber and polymers, it is presently preferred that pusher wire 10 be stainless steel or nitinol. Helical coil 100 likewise can be made of any conductive substance with the appropriate mechanical characteristics. It is presently preferred that helical coil 100 be of the same material as pusher wire 10. Non-conductive bushing 50 may optionally be included at the distal end of insulating layer 20 to provide additional isolation of electrolytic detachment site 30 from helical coil 100. Detachment site 30 is coupled to embolic assembly 120 by another conductive substance that has a different standard electrode potential ($E^0$) than that of detachment site 30. In FIG. 1, the conductive substance is shown as a wire helically-wound around detachment site 30. This, however, is not to be construed as the only way to connect embolic assembly 120 and the delivery device. Any manner of connection such as wire winding, spot welds, pressure clips, etc. that permit close contact of the first conductive substance of detachment site 30 and the second conductive substance will suffice.

As shown in FIG. 1, helical coil 70 is wound around the distal end of electrolytic detachment site 30 and partially encased in a mass of non-conductive substance 80. Non-conductive substance 80 can be any insulating substance, fusable polymers being particularly useful with PET being presently preferred. The proximal end of embolic assembly 120 is also encased in non-conductive substance 80. Upon delivery of an electrical signal to separation locus 30, the conductive substance with the lower $E^o$ will erode away resulting in release of embolic member 120. As shown, connector 70 is a conducting metal that has a different $E^o$ than the metal of which detachment site 30 is comprised. While any two metals that have the required $E^o$ difference may be used, it is presently preferred that separation locus 30 be stainless steel or nitinol and connector 70 be a platinum/tungsten alloy.

Figure 2:
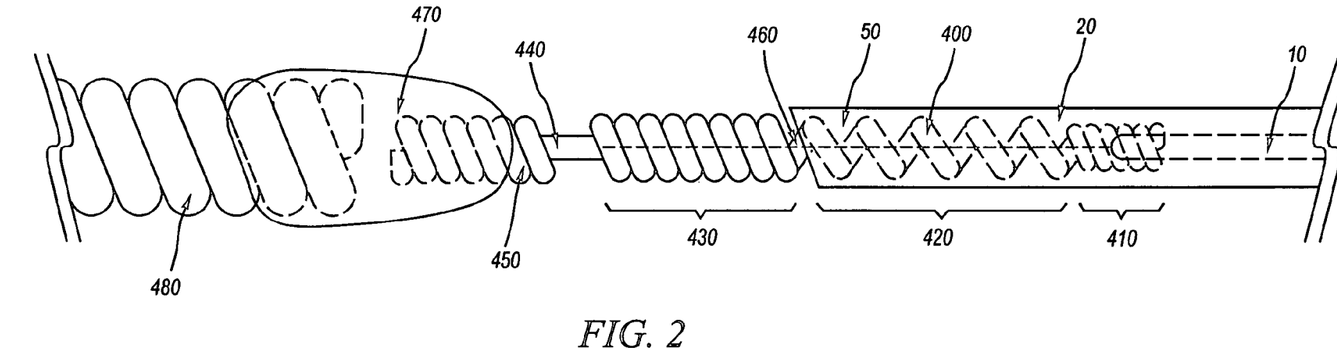
FIG. 2 is a schematic depiction of an embodiment of this invention wherein flexibility is introduced between distal end of pusher wire 10 and embolic member 480 by a helically wound wire comprised of two portions, 420 and 430, which are independently open or closed-pitched.
Figure 3:
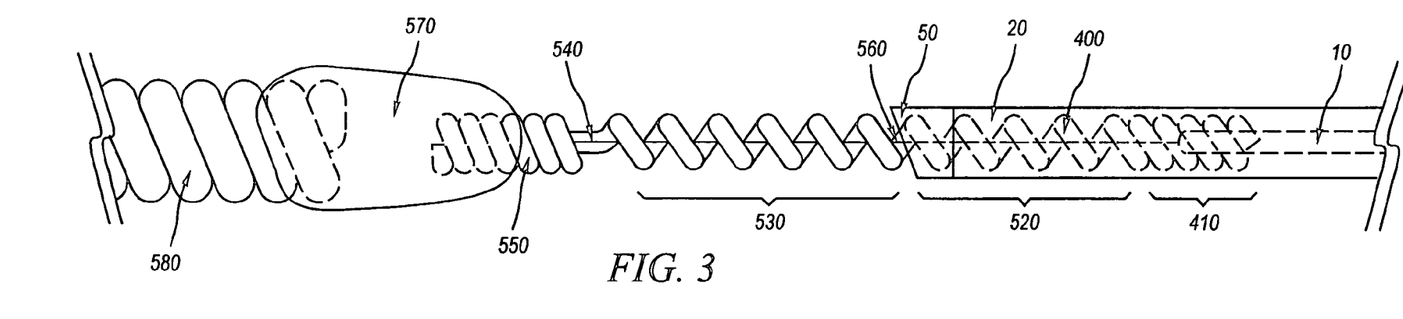
FIG. 3 is a schematic depiction of the embodiment shown in FIG. 2 wherein both the proximal portion 520 and the distal portion 530 of the helically wound segment are open-pitched.

Yet another embodiment of the present invention is schematically depicted in FIG. 2. Pusher wire 10 is coupled to helically-wound segment 410 of wire 400. Segment 420 of wire 400 is open-pitched helically wound. Pusher wire 10, segment 410 and segment 420 of wire 400 are encased in non-conductive substance 20. As in the above embodiments, a non-conductive bushing 50 may be attached to the distal end of non-conductive substance 20 to further isolate open-pitched segment 420 of wire 400 from closed-pitched segment 430 of wire 400. Segment 430 is optionally coated with a non-conductive substance, which may be the same substance used to encase pusher wire 10 and segment 420 or it may be a different non-conducting substance. It should be noted that, as used herein, the term "encased" refers to the complete surrounding of an element of this invention such that the individual features of the element are not readily apparent from the outside of the encasing substance. Thus, the helically-wound nature of a wire encased in a substance would not be apparent to the casual observer. To the contrary, when the term "surface-coated" is used, it means that the element so-coated retained its appearance; i.e., a surface coated helically-wound wire appears to the casual observer as a helically wound wire. A typical example of "surface-coated" would be a common insulated electrical wire available for purchase at a hardware store. Pliable non-conductive materials such as those disclose above with regard to the first embodiment of this invention are presently preferred. The distal end of segment 430 is bare and comprises detachment site 440. The proximal end of helical coil 450 is tightly wrapped around the distal portion of separation locus 440 to bind the two together. As above, helical coil 450 and separation locus 440 are made of metals or alloys having different values of $E^o$. While coil 450 and locus 440 can be made of any metals or alloys that exhibit the required difference in $E^o$, it is presently preferred that detachment site 440 be stainless steel or nitinol and helical coil 450 be a platinum/titanium alloy. The distal end of coil 450 is embedded in a fusible, non-conductive polymeric mass 470. The proximal end of embolic assembly 480 is also embedded in polymeric mass 470. Optional stretch-resistant member 460 may be attached at one end to the distal end of pusher wire 10 and at the other end to detachment site 440 and threaded through the lumen described by the coiled segments of wire 400. Member 460 provides stretch resistance to wire 400 in the helical regions. Member 460 may be made of any resilient, non-stretchable material. In general, polymeric materials having the requisite characteristics are most often used. Presently, polypropylene suture material is preferred. It is emphasize that FIG. 2 represents a version of this embodiment of the invention, that is, while segment 420 is shown as open-pitched and segment 430 as closed-pitched, it is entirely possible, and it is within the scope of this invention, that this be reversed, i.e., that segment 420 be closed-pitched and segment 430 be open-pitched. Likewise, both segments can be closed-pitched or open pitched, this latter configuration being shown schematically in FIG. 3. Furthermore, while FIG. 2 shows the point of separation of segments 420 and 430 as coincidently being the distal end of non-conductive substance 20 or, optionally, the distal end of non-conductive bushing 50, such is not necessarily the case. That is, the distal end of non-conductive substance 20 (or bushing 50) may be anywhere along the length of segment 420 or segment 430. In addition, as is noted above, segment 430 and detachment site 440 are shown being coupled to embolic assembly 480 by helically-wound wire 450 and non-conductive substance 450. There are, however, many ways that this connection can be made give and such will become apparent to those skilled in the art based on the disclosures herein. All such configuration are within the scope of this invention.

Figure 4:
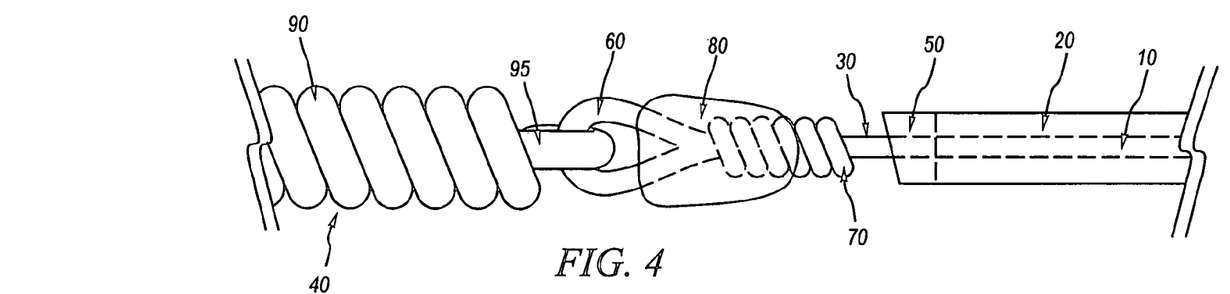
FIG. 4 is a schematic depiction of a further embodiment of this invention wherein flexibility is conferred on the distal end of the device by virtue of interlinked loops 60 and 95.

FIG. 4 depicts yet another embodiment of this invention in which increased flexibility is introduced into the device by means of interlinking loops 60 and 95. Again, pusher wire 10 is encased in non-conductive substance 20, with enough of wire 10 being left exposed at its proximal end to attach to a power supply. In addition, a portion of its distal end is also left bare to provide detachment site 30. Non-conductive substance can be any of those discussed above with regard to the other embodiments of this invention. And again, a non-conductive bushing 50 may optionally be included to provide additional separation of the encased portion of pusher wire 10 from detachment site 30. Electrolytic separation of embolic member 120 is accomplished by virtue of connecting entity 70, which comprises a metal having a different $E^o$ than that of pusher wire 10. Upon delivery of an electrical signal to detachment site 30, the metal with the lower $E^o$ will erode away resulting in release of embolic member 120. As shown, embolic member 120 is attached pusher wire 10 by a mass of non-conducting substance 80, which may be the same as, or different than, the non-conducting substance that is used to encase pusher wire 10. While any combination of metals for core wire 10 and connector 70 that have the requisite difference in $E^o$ may be used, typically core wire 10 is stainless steel or nitinol and connector 70 is a platinum/zirconium alloy.

Eyelet loop 60 can be made of any non-conductive material. Presently preferred are those that can form a fiber or fiber-like structure. PET is a presently preferred substance with the desired characteristics. Embolic assembly member 40 has a distal helically wound coil region 90 and an eyelet loop 95, which is interlinked with eyelet loop 60. As above, the embodiments shown in FIG. 4 are exemplary only and other configurations are possible without exceeding the scope of this invention. For example, region 90 of embolic assembly 40 need not necessarily be a helically-wound wire but may simply be, for example without limitation, a straight segment of wire or even a flat piece of metal.

Figure 5:
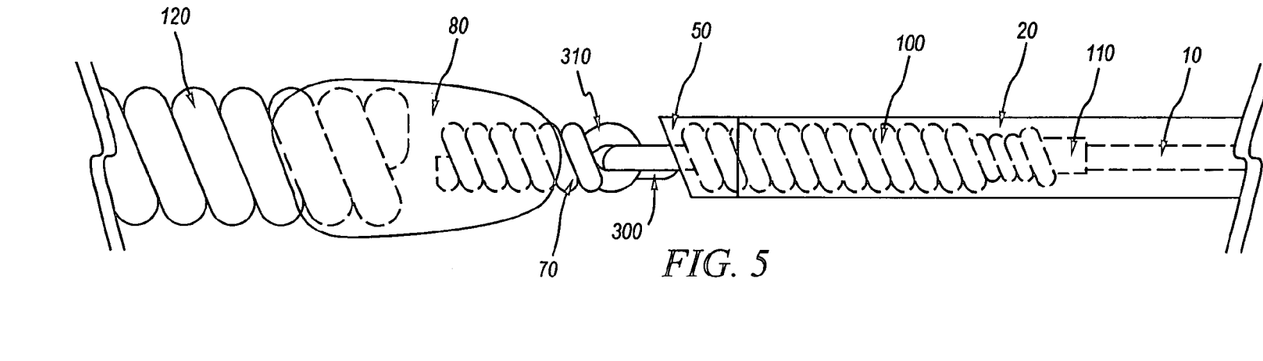
FIG. 5 is a schematic depiction of a still further embodiment of this invention wherein the flexibility-conferring features of the device in FIGS. 1 and 4 are combined; that is, the device in FIG. 5 comprises both a helically wound segment 100 and interlinked loops, 300 and 310.

FIG. 5 is a schematic representation of yet another embodiment of this invention that combines the elements of the two embodiments above. Thus, the distal end of pusher wire 10 is coupled to the proximal end of helical coil 100 by weld junction 110. Helical coil 100 may be open or closed pitch, and the pitch itself may be varied, to establish a desired degree of softness or pliability. Pusher wire 10, weld junction 110 and helical coil 100 are encased in non-conductive substance 20. Non-conductive substance 20 can be any of the materials mentioned above with regard to the first and second described embodiments of this invention or any other material that meets the requirements of the disclosures herein. Likewise, non-conductive bushing 50 may optionally be included at the distal end of insulating layer 20 to provide additional isolation of eyelet loop 300, whereat electrolytic separation of embolic assembly 120 will occur. Coil 70 and eyelet loop 310 are made of an electrically-conductive substance, preferably a metal or alloy that has a different E° from the substance, also preferably a metal, of which eyelet loop 300 is made. While any combination of metals or alloys that has the required difference in E° may be used, it is presently preferred that eyelet loop 300 be stainless steel and that eyelet loop 310 be a platinum/titanium alloy. Helical coil 70 is embedded in a mass of non-conductive substance 80. Also embedded in substance 80 is the proximal end of embolic assembly 120. Substance 80 can be any non-conductive material that can be melted or fused to encase the distal end of coil 70 and the proximal end of assembly 120. A polymeric material, in particular PET, is presently preferred.

CONCLUSION

The specific embodiments of the device set forth herein for improving the flexibility of the distal end of an embolic device delivery apparatus are provided for the purpose of illustration only and are not intended, nor should they be construed, to limit the invention herein in any manner whatsoever. Many alterations and modifications of the device herein will become apparent to those skilled in the art based on the disclosures herein; all such alterations and modifications are within the scope of this invention.

What is claimed:

1. A device for releasing an embolic assembly at a target site in a vessel of a patient, comprising:
    a core wire comprising a first electrically-conductive substance that is at least partially fixedly encased in a first non-conductive substance and has a proximal and a distal end, its proximal end being configured to be connected to an electrical signal generator;
    a flexible member configured for permanent attachment to the core wire, the flexible member having a proximal and a distal end, its proximal end being coupled to the distal end of the core wire, the flexible member comprising a second wire comprising a second electrically-conductive substance, which may be the same as, or different than, the first electrically-conductive substance, the second wire having a helical coil segment fixedly coupled to the distal end of the core wire and being fixedly encased in the first non-conductive substance, and a straight segment located distal to the helical coil segment, at least a portion of the straight segment comprises a bare comprising an electrolytic detachment site;
    an electrically conductive, helically-wound wire fixedly secured to the bare portion of the straight segment, wherein a distal portion of the electrically conductive, helically-wound wire is embedded in a polymeric mass;
    an embolic assembly having a proximal and a distal end, its proximal end being embedded in the polymeric mass, the polymeric mass coupling the electrically conductive, helically-wound wire to the proximal end of the embolic assembly; and
    wherein the helically wound segment of the second wire comprises a first and a second helically wound portion, the first portion being one of open-pitched or closed-pitched and the second portion being the other of open-pitched or closed-pitch, the first portion being at least partially fixedly encased in the first non-conductive substance and being coupled to the distal end of the core wire, the second portion optionally being partially encased in the first non-conductive substance and distal to the first portion and coupled to the straight segment.

2. The device of claim 1, wherein the electrically conductive, helically-wound wire fixedly secured to the bare portion of the straight segment is, along with the proximal end of the embolic assembly, encased in a non-conductive substance that may be the same as, or different than, the first non-conductive substance.

3. The device of claim 1, wherein the first portion of the helically wound segment is open-pitched and the second portion is closed-pitched.

4. The device of claim 1, wherein the second portion of the helically-wound segment is at least partially surface-coated with a second non-conductive substance, which may be the same as, or different from, the first non-conductive substance.

5. The device of claim 1, wherein:
    the core wire comprises stainless steel or nitinol;
    the first non-conductive substance comprises a first non-conductive polymer;
    the second wire independently comprises stainless steel or nitinol; and,
    the electrically conductive, helically-wound wire fixedly secured to the bare portion of the straight segment comprises a platinum-tungsten alloy.

6. The device of claim 1, further comprising a non-conductive bushing at a distal end of the first non-conductive substance, the bushing having a lumen through which the distal end of the core wire, or the distal end of a flexible member, passes.

7. The device of claim 1, wherein the target site is selected from the group consisting of an aneurysm, an arteriovenous malformation, a fistula, a blood vessel or any other body lumen.

8. The device of claim 1, wherein the first portion of the helically wound segment is closed-pitched and the second portion is open-pitched.

9. The device of claim 1, further comprising a stretch resistant member having a first end and a second end, the first end being fixedly coupled to the distal end of the core wire and the second end being fixedly coupled to the flexible member.

10. A method for releasing an embolic assembly at a target site in a patient's body, comprising:
    providing a delivery member capable of positioning a core wire in close proximity to a target site, the delivery member comprising a first elongate tube having a proximal end, a distal end and an axial lumen;
    providing a core wire slidably disposed within the axial lumen, the wire comprising a first electrically-conductive substance that is at least partially fixedly encased in a first non-conductive substance and has a proximal and a distal end, its proximal end being configured to be connected to an electrical signal generator;
    providing a flexible member configured for permanent attachment to the core wire, the flexible member comprising a second wire formed from a second electrically-conductive substance, which may be the same as, or different than, the first electrically-conductive substance, the second wire having a helical coil segment comprising first and second helically wound portions, the first portion being one of open-pitched or closed-pitched and the second portion being the other of open-pitched or closed-pitch, the first portion being at least partially fixedly encased in the first non-conductive substance and being coupled to the distal end of the core wire, the second portion optionally being partially encased in the first non-conductive substance, the second portion being distal to the first portion, the flexible member further comprising a straight segment located distal to the helical coil segment, at least a portion of the straight segment being bare and comprising an electrolytic detachment site;

providing an electrically conductive, helically-wound wire fixedly secured to the bare portion of the straight segment, wherein a distal portion of the electrically conductive, helically-wound wire is embedded in a polymeric mass;

providing an embolic assembly having a proximal and a distal end, its proximal end being embedded in the polymeric mass, the polymeric mass coupling the electrically conductive, helically-wound wire to the proximal end of the embolic assembly; and, moving the delivery member to a position in close proximity to the target site;

sliding the core wire through the lumen of the delivery member until the embolic assembly is at or in the target site; and, sending an electrical signal to the electrolytic detachment site which results in release of the embolic assembly.

11. The method of claim 10, wherein the first portion of the helically wound segment is open-pitched and the second portion is closed-pitched.

12. The method of claim 10, wherein the second portion of the helically-wound segment is at least partially surface-coated with a second non-conductive substance, which may be the same as, or different from the first non-conductive substance.

13. The method of claim 10, further comprising a stretch resistant member having a first and a second end, the first end being fixedly coupled to the distal end of the core wire and the second end being fixedly coupled to the flexible member.

14. The method of claim 10, further comprising a non-conductive bushing coupled to a distal end of the first non-conductive substance and having a lumen through which the distal end of the core wire, or the distal end of the flexible member, passes.

15. The method of claim 10, wherein the target site is selected from the group consisting of an aneurysm, an arteriovenous malformation, a fistula, a blood vessel or any other body lumen.

16. The method of claim 10, wherein the first portion of the helically wound segment is closed-pitched and the second portion is open-pitched.

* * * * *

UNITED STATES PATENT AND TRADEMARK OFFICE
CERTIFICATE OF CORRECTION

| | | |
|---|---|---|
| PATENT NO. | : 7,651,513 B2 | Page 1 of 1 |
| APPLICATION NO. | : 10/407295 | |
| DATED | : January 26, 2010 | |
| INVENTOR(S) | : Kevin M. Jaeger et al. | |

It is certified that error appears in the above-identified patent and that said Letters Patent is hereby corrected as shown below:

In the front page, number (12) First inventor, delete "Teoh et al." and insert therefore -- Jaeger et al. --

In the front page, number (75) Inventors, the order of inventors is shown as follows:

Kevin M. Jaeger, Pleasanton, CA (US);

Stephen C. Porter, Oakland, CA (US);

Clifford Teoh, Los Altos, CA (US);

Michael Wallace, Fremont, CA (US);

Maria Pizarro, Union City, CA (US)

Signed and Sealed this

Twenty-seventh Day of April, 2010

David J. Kappos
*Director of the United States Patent and Trademark Office*

UNITED STATES PATENT AND TRADEMARK OFFICE
CERTIFICATE OF CORRECTION

PATENT NO.      : 7,651,513 B2                                       Page 1 of 1
APPLICATION NO. : 10/407295
DATED           : January 26, 2010
INVENTOR(S)     : Kevin M. Jaeger et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1652 days.

Signed and Sealed this

Twenty-third Day of November, 2010

David J. Kappos
*Director of the United States Patent and Trademark Office*